United States Patent [19]

Bemurat

[11] Patent Number: 5,480,419
[45] Date of Patent: Jan. 2, 1996

[54] STIMULATION LEAD SPECIALLY CARDIAC WITH AUXILIARY CONNECTION

[76] Inventor: Marc F. Bemurat, 20 Allées du Bicon, F-33850 Leognan, France

[21] Appl. No.: 339,286

[22] Filed: Nov. 7, 1994

Related U.S. Application Data

[63] Continuation of Ser. No. 978,762, Nov. 19, 1992, abandoned.

[30] Foreign Application Priority Data

Dec. 17, 1991 [FR] France ................... 91 15903
Oct. 6, 1992 [EP] European Pat. Off. ............. 92450013

[51] Int. Cl.⁶ .................................................. A61N 1/04
[52] U.S. Cl. .......................................... 607/115; 128/642
[58] Field of Search ...................... 439/271, 588, 439/909; 128/642; 604/21, 27, 23; 607/96, 98, 99, 103, 106, 113, 115, 117, 119, 122, 125, 127, 128, 132, 133, 148, 156

[56] References Cited

U.S. PATENT DOCUMENTS

| 3,924,639 | 12/1975 | Hess | 607/122 |
|---|---|---|---|
| 4,154,247 | 5/1979 | O'Neill | 128/419 P |
| 4,317,459 | 3/1982 | Gilman | 607/126 |
| 4,499,907 | 2/1985 | Kallok | 128/786 |
| 4,644,960 | 2/1987 | Johans | 607/122 |
| 5,111,830 | 5/1992 | Bemurat | 128/786 |

FOREIGN PATENT DOCUMENTS 0396835  11/1990  European Pat. Off. .

Primary Examiner—William E. Kamm
Assistant Examiner—Marianne Parker
Attorney, Agent, or Firm—Roylance, Abrams, Berdo & Goodman

[57] ABSTRACT

A pacemaker lead includes a spiral electrical conductor lead surrounded by an insulating material sheath. One end of the lead is coupled to a connection head for removable connection to a pacemaker. The other end of the lead is connected to a stimulation device. Between the ends, the lead has a sealed access structure housing an auxiliary electrical connection for electrically coupling an external stimulation source or other circuit to the conductor lead by movement across the access structure.

19 Claims, 2 Drawing Sheets

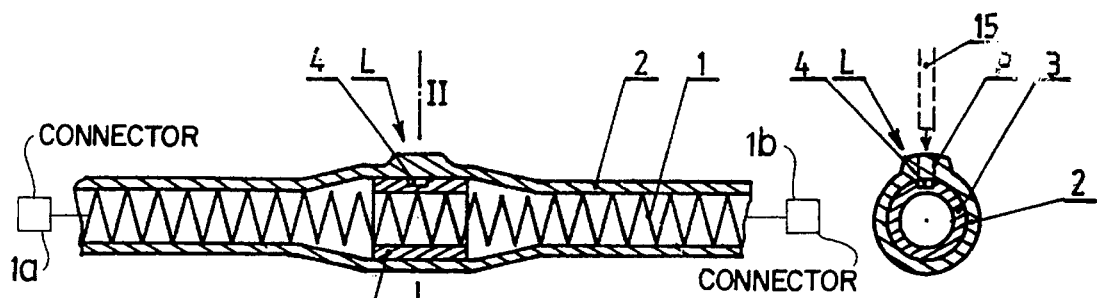
FIG.1.
FIG.2.
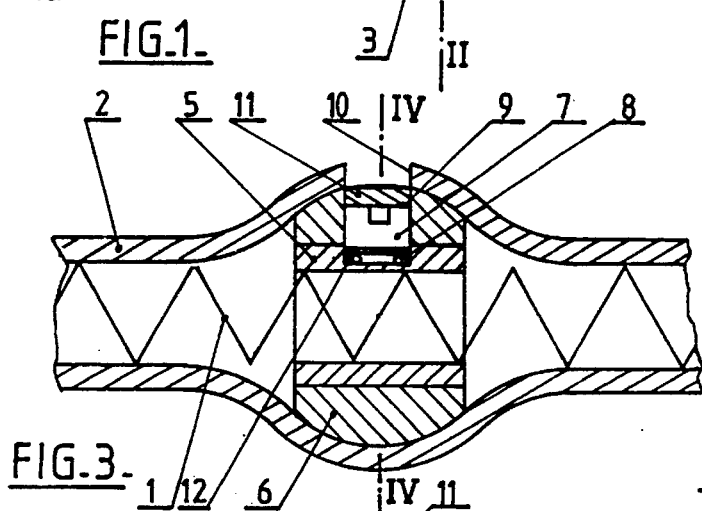
FIG.3.
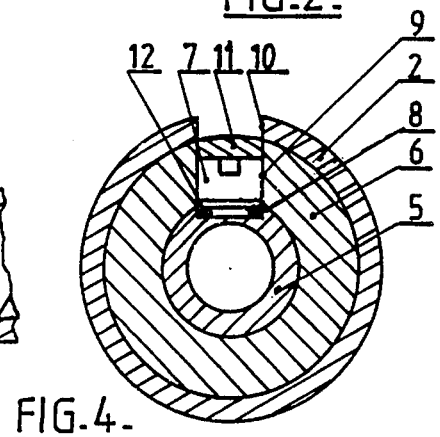
FIG.4.
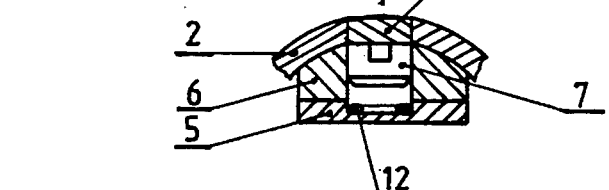
FIG.5.
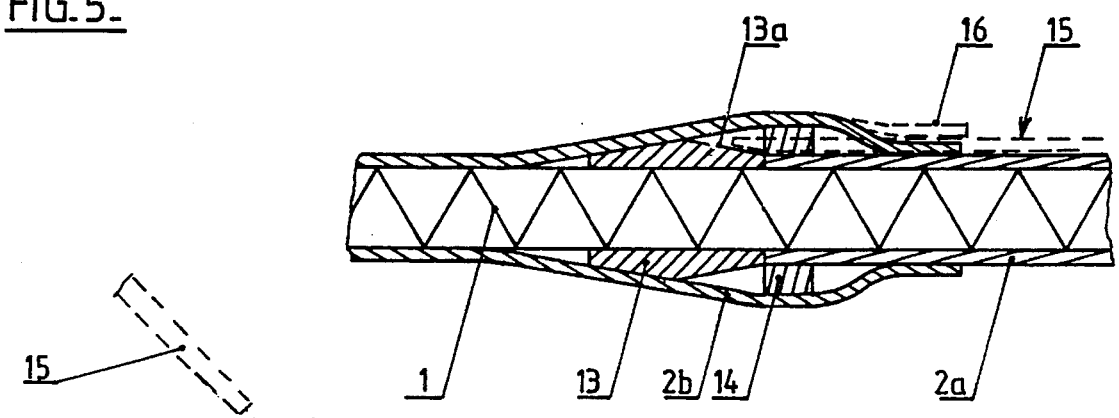
FIG.6.
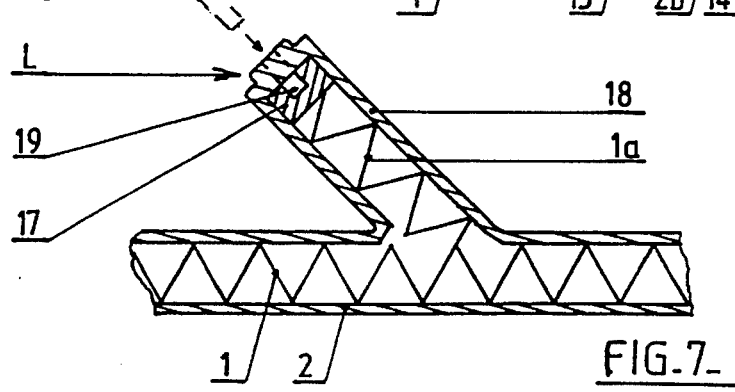
FIG.7.

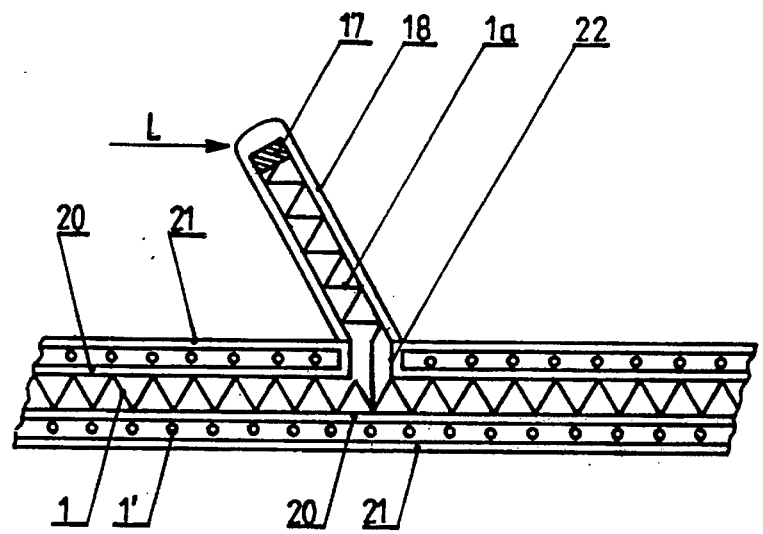
FIG. 8.
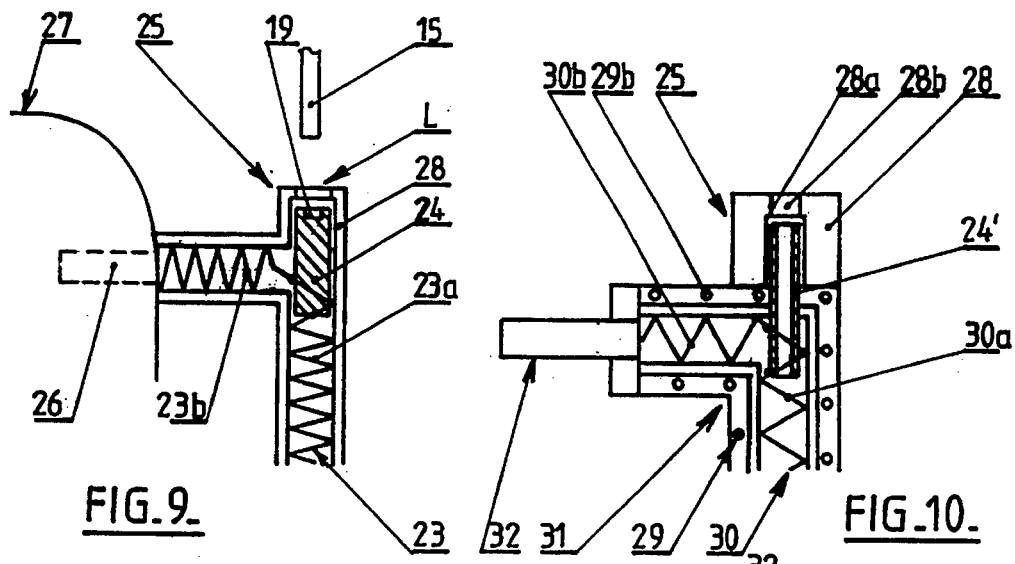
FIG. 9.
FIG. 10.
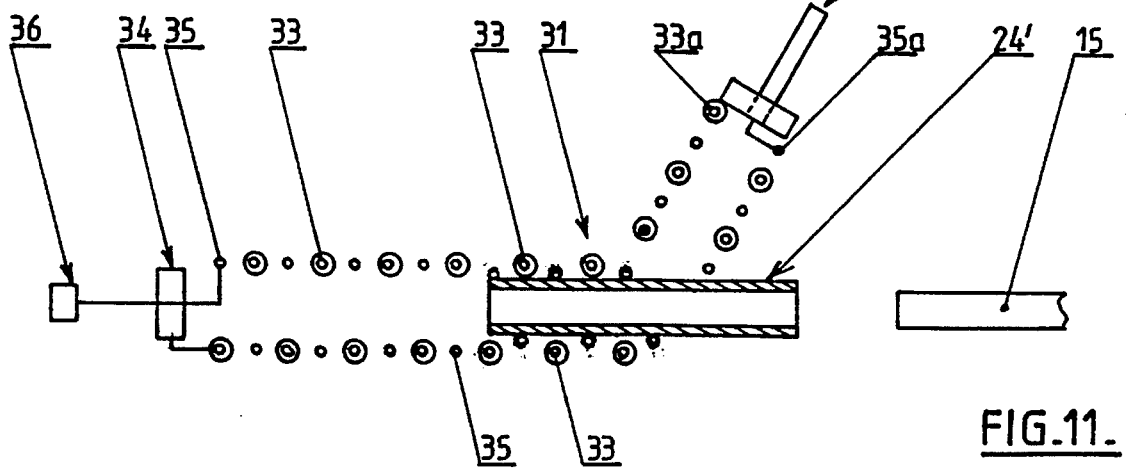
FIG. 11.

STIMULATION LEAD SPECIALLY CARDIAC WITH AUXILIARY CONNECTION

This is a continuation of application Ser. No. 07/978,762, filed Nov. 19, 1992, now abandoned.

BACKGROUND OF THE INVENTION

FIELD OF THE INVENTION

The present invention relates principally but not exclusively to pacemaker stimulation leads.

Presently, only the head of the lead can receive electrical stimulation. This lead head introduced into the pulse generator is accessible only when the lead is disconnected and removed from the pulse generator.

The stimulation lead is practically always kept in place during replacement of a pulse generator. The manoeuver consists of disconnecting the lead from the pulse generator, removing it therefrom, reintroducing it into the new pulse générator and finally, reinserting the lead and pulse generator assembly under the skin.

This handling can require several tens of seconds.

In this case, as soon as the lead is disconnected, the patient is no longer being stimulated. This is no problem if the patient maintains a minimus of spontaneous cardiac rhythm, but some "dependent" patients have no spontaneous rhythm at all. They are then in cardiac arrest until the moment when the stimulation lead is connected to the new pulse generator.

In a dependant patient, then, the manoeuver is delicate, even dangerous.

One type of pacemaker lead with auxiliary stimulation pole is already known from French Patent 2,654,939, filed in the name of the Applicant, in which a break is provided in the strand sheathing reaching from the pacemaker to the electrode device for stimulation, making the lead conductor(s) accessible from the outside, the break possibly being insulated from the outside by a movable means such as a sleeve mounted sliding on said strand.

Despite the advantages in a practical sense of a movable covering sleeve, intended to mask the break in the insulated and protective sheathing of the internal conductor(s), can in time pose sealing problems and thus problems with the insulation of the conductor(s) vis-a-vis the medium surrounding the lead, which is a conductive medium and which could establish short-circuits between said conductor(s) and the pacemaker pulse generator.

SUMMARY OF THE INVENTION

The object of the present invention when applied to pacemaker lead is precisely to eliminate such a risk, even as minimal and theoretical as it is, by proposing new provisions adapted to assure the most perfect tightness possible.

For this, the object of the invention is a stimulation lead, specially a pacemaker lead, with an auxiliary electrical connection, of the type comprising a flexible strand constituted of at least one spiral electrical conductor surrounded with a sheathing of insulating material and connected at one end of the lead to a removable connection head from the pulse generator and at the other end of the lead to an electrode stimulation device, said lead comprising:

a sealed access structure to said electrical conductor, and, a means of auxiliary electrical connection to assure the electrical connection between said conductor and an external stimulation source or other circuit, by direct physical contact by movement across said access structure.

The sealed access structure is preferably constituted of a piece made of an electric conducting material covered with a sealed covering structure, said auxiliary electrical connection means being able to traverse said covering structure.

In the present description, strand refers to the connecting member between the electrode(s) stimulation device and the pulse generator or analogous, whether this connection is constituted of one single strand or of a strand connected by any interconnection means to a juncture called adaptor and provided with an appropriate head, the device of the invention being provided on the single strand or on said adaptor.

In a first embodiment, said piece made of an electric conducting material is a sleeve covered by an outside sheathing provided with a lens which is traversable in a sealed manner, facing the sleeve, said electric connection means being constituted of a separate electric conducting rod of which the end is structured in an appropriate manner and is received in the lodging of the sleeve which is also of an appropriate shape.

In a second embodiment, said piece made of an electric conducting material is a sleeve partially covered by the external sheathing, said connection means constituted on the one hand of a screw of electrically conductive material engaged in a hole arranged in the sheathing and in a rigid electrically insulating material placed between the sheathing and the sleeve, the screw capable of being screwed into contact with the sleeve without breaking the seal between the inside and the outside of the sheathing, and on the other hand, of the metal rod of a screwdriver or the like.

In this latter embodiment, said screw can be bareheaded or else covered with a patch of elastic material which can be traversed in a sealed manner.

In a third embodiment, said piece made of an electric conducting material is a sleeve and the covering means is constituted of a part of the sheathing forming an encasing sleeve and optionally of a ring of elastic material traversable in a sealed manner, while the electric connection means is constituted of an independent metal rod.

In a fourth embodiment, said piece made of an electric conducting material is a derivation connected to an end piece made of an electric conducting material, the entirety covered with an insulating covering constituted of a sheathing and a lens which can be traversed in a sealed manner, positioned in regard of the end piece, and the electric connection means is constituted of an independent metal rod.

In a fifth embodiment, the electrical conductor of the lead makes an elbow at the level of which said piece made of an electric conducting material is in contact with the conductor, the piece made of an electrical conducting material provides a derivation coaxial with the part of the conductor facing said stimulation electrode, is able, at its free end, to receive said auxiliary electrical connection means and is covered with said covering structure.

In such an embodiment, the auxiliary electrical connection means can be the rod of a screw-driver, but also the metallic stilet for inserting the lead in the heart.

Moreover, the invention is applicable to unipolar leads as well as to bipolar leads comprising two spiral electric conductors, side by side or coaxial, of equal diameter (multicoiled bipolar lead) or of different diameter, one of said spiral conductors being housed within the other one.

The invention is also applicable to implantable defibrillator leads, providing thus, through such an auxiliary electric connecting pole, the possibility of triggering a ventricular arrhytmia by stimulating the distal electrode. The invention also applies to anti-tachycardia pacemakers and, generally speaking, to any implantable lead, cardiac or not, mono or multicoiled, and enables with such a lead either to apply stimuli or an electric potential, or to collect electrical signals from the lead, whether the lead installation is disconnected or not.

BRIEF DESCRIPTION OF THE DRAWINGS

Other characteristics and advantages will arise from the following description of embodiments of the device, the description provided solely as an example and relating to the attached drawings, wherein:

FIG. 1 is a longitudinal axial section of a lead of the invention according to a first embodiment;

FIG. 2 is a transverse section along line II—II of FIG. 1;

FIG. 3 is a longitudinal axial section of a lead of the invention according to a second embodiment;

FIG. 4 is a transverse section along line IV—IV of the lead of FIG. 3;

FIG. 5 is a partial view of the lead of FIG. 3 illustrating a non-contact position of the electric connection screw;

FIG. 6 is a longitudinal axial section of a lead of the invention according to a third embodiment;

FIG. 7 is an axial section of a lead with a bifurcation or derivation according to the invention;

FIG. 8 is a view illustrating the application of the derivation lead of FIG. 7 to a lead comprising two coaxial spiral conductors of unequal diameter;

FIG. 9 is a schematic view of a fifth embodiment;

FIG. 10 is a schematic view of a sixth embodiment; and

FIG. 11 is a schematic view of a seventh embodiment.

DETAILED DESCRIPTION OF THE INVENTION

FIGS. 1 and 2 show an unipolar lead for cardiac stimulation, constituted, as is known, of an electric conductor 1 wound in a spiral with essentially joined spires and surrounded with a sheathing 2 of flexible electrically insulating and biocompatible material.

In the known manner, conductor 1 is connected at one end to a tubular male contact 1a intended to come into electric contact with the internal circuits of a pulse generator and, at the other end, to a single or double electrode excitation device (1b).

In the invention, conductor 1 is surrounded by a sleeve 3 made of an electric conducting material, such as a metal or alloy, soldered to conductor 1 and in turn encased completely by a sheathing 2. A hollowed-out impression 4, for example of hexagonal shape, is worked on the external surface of conductor 3, in the appropriate manner intended to receive the end of a metal rod which can serve as electrical connection between internal conductor 1 and an external source of stimulation, or an auxiliary stimuli generator; intended to carry the relay of the pacemaker installation temporarily at the moment of disconnection of the latter for pulse generator replacement.

Said metal rod passes through sheathing 2 to realize the electrical connection.

For this, a bulge in the form of a lens L is worked in the wall of sheathing 2, which is preferably of silicon, opposite to impression 4.

Lens L is a simple local extrathickness and is provided with a passage on either side (shown as a P in FIG. 2) which is normally blocked and sealed by the elasticity of the material. Such an arrangement is already known and used in silicon casings for pulse generator, opposite connection screws of the lead, and allows access to these screws by means of a screwdriver without causing damage to the seal of the casing.

Generally speaking, in the present description, lens will mean any zone constituted of a material, either identical to the material of surrounding sheathing 2 or not, which can be traversed in a sealed manner by a rod or the like. In other words, after withdrawal of the rod, the material is capable of recovering its entire tightness, the passage hole of the rod reclosing on itself as a result of the elasticity of the material.

The end of a screwdriver 15 or similar device (FIG. 2) can be engaged to connect sleeve 3, in other words conductor 1, to an external stimuli source, and the end of screwdriver 15 is shaped to correspond with impression 4, which is the case of screwdriver(s) traditionally used to connect a pulse generator to a lead, across lens L, by virtue of passage P preformed in the latter facing impression 4 and reaching as far as contact with sleeve 3.

The elastic check of the material of sheathing 2 holds the rod of screwdriver 15 in contact with sleeve 3, even if the screwdriver is released. The electric connection between the rod part of the screwdriver and the external stimulation source is realized for instance by the interposition of an alligator clip.

Upon withdrawal of the rod part of screwdriver 15, passage P preformed in lens L and sheathing 2 recovers its entire tightness of fit.

In the embodiment shown in FIGS. 3 to 5, internal spiral conductor 1 is also soldered to an external sleeve 5 made of an electric conducting material, sleeve 5 being surrounded by a sleeve 6 of rigid electrically insulating material, for example a plastic. Sleeve 6 is covered by lead sheathing 2, for example of silicon.

The electric contact between sleeve 5 and the external stimulation source is controlled by means of an electric conducting screw 7 lodged in a threaded hole arranged radially around the lead. This hole comprises a part 8 in the external surface of sleeve 5 and which does not pass through the latter, a part 9 on the other side of the wall of insulating sleeve 6 and a part 10 passing through sheathing 2.

The head of screw 7 in the embodiment shown is covered with a cylindrical patch 11 of silicon or the like, optionally provided with a preformed passage analogous to that of lens L of the embodiment of FIGS. 1 and 2. Patch 11 blocks part of hole 10 when screw 7 (FIG. 3) is sufficiently distant from metal sleeve 5 to no longer be in contact with it.

An annular washer 12 forming abutment for screw 7 is placed in the bottom of hole 8 to provide a chamber of compressed air between the latter and electric conduting sleeve 5, when the screw (FIG. 4) is screwed to the bottom, establishing contact between screw 7 and sleeve 5.

Engagement of a rod of a screwdriver through patch 11 allows screw 7 to be screwed (FIG. 4) to establish an electric connection via sleeve 5, screw 7 and the screwdriver, between conductor 1 and an auxiliary stimulation lead, or on the contrary to electrical insulate screw 7 from sleeve 5, in terms of a total insulation.

It is to be noted that patch 11 can be deleted if desired, whereby the head of screw 7 is then bare.

The embodiment of FIG. 6 comprises a different structure of elastic material traversable in a sealed manner appropriate to assure a temporary electrical connection between the internal spiral conductor of the lead and the exterior.

In this FIG. 6 embodiment, internal spiral conductor 1 is soldered to an external sleeve 13 made of an electric conducting material. The sheathing is separated into two segments, segment 2a coming into engagement against sleeve 13 and segment 2b covering both sleeve 13 and the end of segment 2a.

Said traversable structure is constituted of an annular element 14 of an elastic material such as silicon, interposed between the overlapping covering parts of the segments 2a, 2b. Element 14 is formed for example of a ring with one or more passages parallel to the axis of conductor 1, preformed therein, in the manner of the aforementioned lens L.

Element 14 can be formed of segments placed annularly side by side, each segment being provided with a preformed passage parallel to the axis of the conductor.

The part of segment 2b covering ring 14 lies flat against the latter and also against segment 2a by the effect of elasticity. For improved tightness, ring 14 is soldered to sheathing parts 2a, 2b.

The external surface of sleeve 13 is advantageously biconical in order to constitute an inclined surface 13a, assuring contact with the end of a metal rod 15, for example a screwdriver, engaged under the free end 16 of segment 2b, so surface 13a.

Rod 15 allows for temporary electric connection between conductor 1 and an auxiliary stimulation source.

Following removal of rod 15, the overall tightness of the material of the device is restored.

Inclined surface 13a, by its wedge effect, contributes to improved contact between sleeve 13 and rod 15.

It is to be noted that ring 14 could be deleted, and then the structure which is traversable in a sealed manner by vertue of the access to metal sleeve 13 then being formed by the overlapping of the two segments 2a, 2b, the elastic constriction effect exerted by sheathing 2b on sheathing 2a beneath it assuring the desired tightness while also allowing the insertion of rod 15 in order to come into contact with sleeve 13.

FIG. 7 illustrates still another embodiment in the form of a Y forming a derivation, with the aid of a segment of the spiral conductor of which one of the ends is soldered to conductor 1 and the other end is soldered to a connection stud 17.

The entirety of derivation 1a, 17 is covered with a sheathing 18 similar to sheathing 2 of the lead. The end surface of the derivation is provided with an extrathickness or lens L, provided with a preformed passage (not shown in FIG. 7) analogous to that of lens L of FIG. 2 and facilitating the passage of a rod without damage to the tightness of the material of the wall being passed through, following withdrawal of the rod.

An impression 19 to receive the end of a metal rod, for example a screwdriver 15, is advantageously arranged on the external surface of stud 17 for improved contact, as in the case (impression 4) of the embodiment of FIGS. 1 and 2. Metal rod 15 permits temporary electrical connection between conductor 1 and an auxiliary stimulation source.

FIG. 8 illustrates the application of the derivation principle of FIG. 7 to a bipolar lead with two coaxial spiral electric conductors, 1 and 1' respectively, the one (1) being within the other (1').

The smallest diameter conductor 1 is connected for instance to the distal stimulation electrode when the other conductor 1' is connected to the nearby stimulation electrode.

Conductors 1, 1' are separated by an insulating sheathing 20, the outer conductor 1' is covered with an insulating sheathing 21, the central conductor 1 is electrically connected to a derivation section 1a surrounded by a sheathing 18 and the end of said dérivation section 1a is welded to said connecting stud 17 covered with said extrathickness or lens L.

To make electric insulation between conductors 1, 1' the connection between conductor 1 and section 1a is surrounded with an insulating sleeve 22, at the level of conductor 1'.

The device of FIG. 8 is used as that of FIG. 7.

The devices of FIGS. 1 to 6 are of course applicable to bipolar leads of the concentric spiral type of FIG. 8. To this end, sleeves 3,5,13 are connected to the outer conductor which corresponds to conductor 1 of FIGS. 1 to 6. Said outer conductor, which is connected to the proximal stimulation electrode, is sufficient to apply an appropriate temporary stimulation. Said sleeves 3, 5, 13 could be also connected, in such bipolar leads, to the inner conductor, an electric insulation being provided at the level of the traversing of the outer conductor.

FIG. 9 illustrates a fifth embodiment applied to an unipolar lead, wherein the electric conductor 23 makes an elbow at the level of which said conductor comes into contact with a piece 24 made of an electric conducting material and adapted to form a derivation 25 in the axis of the part 23a of said conductor facing the stimulation electrode, the other part 23b of the conductor, on the other side of the elbow, being connected to the plug 26 connecting the lead to the pulse generator 27.

The piece 24 is provided within the part 23a of the conductor and leaves the spiral conductor 23 to constitute the derivation 25.

At the level of the derivation 25, the piece 24 is covered with an insulating sheath-shaped structure 28, the end of which is provided, as devices of FIGS. 7 and 8, with an extrathickness or lens L made of a material which can be traversed in a sealed manner by a rod 15 of a screwdriver for instance.

The extrathickness or lens L can be replaced by an opening 28a closed by a movable element 28b, as illustrated by FIG. 10.

The piece 24 can be solid and provided at its end with an impression 19 for reveiving the end of the rod 15, as for piece 17.

The piece 24 can also be tubular as illustrated in 24' on FIG. 10 and provided at its outer end, as a female plug to receive the end of the rod 15. Such a tubular piece 24' enables to use, as an auxiliary electric connection, the metal stilet used to put in place the lead within the heart.

To this effect, said stilet is slipped into the tubular piece 24', through lens L, then easily pushed into part 23a of the conductor 23, said part being in the axis of the piece 24'. The stilet thus inserted is in contact with the conductor 23 and can assure a temporary stimulation to the distal electrode of the lead.

The parts 23a and 23b of the conductor 23 can make between then an angle of various value.

All the embodiments shown and described above assure temporary electrical connection between the central conductor of the lead (unipolar, FIG. 1 to 7, or bipolar, FIG. 8) and an external source, in conditions of high reliability and tightness which is of importance for totally satisfaying reutilization of the lead.

The invention of course is not limited to these embodiments but rather covers all modifications, particularly in nature, design, and dimensions of sleeves 3,5,6,13, of connection stud 17, of the derivation piece 24, 24' and of elements which can be traversed in a sealed manner (L, 11,14) which can be interposed between independent metal connection rod 15 and said elements 3,5,13 made of an electric conducting material, stud 17, or piece (24,24') arranged in the interior of the strand and in permanent contact with the internal conductor of the lead.

Particularly, the derivation principle as illustrated on FIG. 9 can apply to bipolar leads.

FIG. 10 illustrates an application to a lead with two concentric coaxial electric conductors, namely an outer conductor 29 connected to the proximal electrode (not shown) in the known manner, and an inner conductor 30 connected to the distal electrode (not shown).

The electrode assembly 29, 30 makes an elbow 31. At the level of said elbow is provided a tubular piece 24' made of an electric conducting material, inserted within the inner conductor 30 in prolongation of the part 30a facing to the distal electrode of said conductor 30.

The piece 24' traverses the outer conductor 29, is electrically insulated with respect to the latter and provides a derivation 25 similar to that of FIG. 9, with an insulating sheath 28 and an end opening 28a closed by a movable element 28b.

The bent parts 29b, 30b of the conductors are connected in the usual manner to a male bipolar plug 32 for connection to a pulse generator (not shown).

This embodiment is used in a manner similar to that of embodiment of FIG. 9, for temporary stimulation of the heart through the distal electrode, element 28b being removed to insert the rod 15 or stilet.

The opening 28a and closing member 28b can be replaced by the extrathickness or traversable lens L of FIG. 9.

FIG. 11 illustrates an application to a bipolar lead with two imbricated spiral conductors of equal diameter.

One (33) of the conductors is insulated and connected to the proximal stimulation electrode 34, when the other (35) is not insulated and is connected to the distal stimulation electrode 36.

The two conductors (33, 35) make an elbow 31, at the level of which a tubular piece 24' made of an electric conducting material traverses the two spiral conductors, by inserting the same within said conductors in prolongation of the parts of the conductors connected to the electrodes (34, 36). The said conductors make a derivation similar to that of FIGS. 9, 10, with an insulating covering (not shown) and an extrathickness or lens L (not shown) in order to access to the tubular piece 24', by way of a rod 15 of a screwdriver or said metal stilet The bent parts (33a, 35a) of the spiral conductors are connected in the usual manner to a bipolar male plug 32 for connection to a pulse generator (not shown).

The device of FIG. 11 is used as that of FIGS. 9 and 10.

The tubular piece 24' of devices of FIGS. 10 and 11 can be of course replaced by the solid piece 24 of FIG. 9.

The piece 24' can also be affixed to the conductor connected to the proximal stimulation electrode, taking into account the necessary insulations between said piece and the other conductor.

The pieces 24 and 24' can be connected to anyone of the two bent conductors of a two parallel spiral conductor lead.

The auxiliary connection pole of the leads according to the invention can be used in any other case where the installation is manoeuvered (reimplanting for instance), whether there is disconnection or replacement or not of said installation.

In application to implantable defibrillator leads provided with three side by side or concentric conductors, the auxiliary connection pole is preferably connected to the distal stimulation electrode conductor. It enables also to check the functionning of the defibrillator.

According to applications, the auxiliary connection pole enables to apply stimuli or an electric potential to conductor or anyone of the conductors of lead of any type, cardiac or not, in substitution to usual stimuli or potentials or superimposition to them, as well as to collect any electric signal from installation or electrode(s).

Finally, in all or some of the embodiments it is possible to delete the piece (3, 5, 13, 17, 24, 24') made of an electric conducting material and provide a direct contact, when the covering structure (2, L, 28) is traversed, between the screwdriver or stilet (15), or analogous, and the electric conductor, or anyone of the electric conductors, of the lead or analogous.

I claim:

1. A pacemaker lead system, comprising:
   a flexible spiral electrical conductor having first and second connector means at opposite ends thereof for removably connecting said conductor to a pulse generator and to an electrode stimulation device, respectively;
   a flexible insulating sheath surrounding said conductor;
   a sealed access means for providing controlled access to said electrical conductor, said sealed access means including a piece of a rigid electrically conducting material, said piece being electrically connected to said conductor;
   a sealed covering structure covering said piece; and
   auxiliary electrical connection means for forming an electrical connection between said piece and an auxiliary electrical circuit, said auxiliary electrical connection means being able to traverse said covering structure and to contact said piece without penetrating material of said piece.

2. A pacemaker lead system according to claim 1 wherein said piece is electrically connected to said conductor by a segment of said conductor forming a derivation, said covering structure surrounding said derivation.

3. A pacemaker lead system according to claim 1 wherein said electrical conductor comprises an elbow where said piece contacts said conductor, said piece providing a derivation in a longitudinal direction of a part of said conductor extending to said second connector means.

4. A pacemaker lead system according to claim 3 wherein said covering structure comprises a prolongation of said sheath, said prolongation having a preformed access opening leading to said piece in said derivation, said opening extending along a longitudinal axis of said derivation and having a movable closing member.

5. A pacemaker lead system according to claim 3 wherein said covering structure comprises a prolongation of said sheath, said prolongation having an end with end material traversable in a sealed manner.

6. A pacemaker lead system according to claim 1 wherein said piece is a massive piece having a lodging at one end thereof; and said auxiliary connection means comprises an independent metal rod received in said lodging of said massive piece.

7. A pacemaker lead system according to claim 1 wherein said piece is a sleeve.

8. A pacemaker lead system according to claim 7 wherein said auxiliary connection means is a stilet for inserting a lead into a patient's heart.

9. A pacemaker lead system according to claim 1 wherein the auxiliary connection means is an independent metal rod.

10. A pacemaker lead system according to claim 1 wherein said covering structure comprises a lens formed as part of said sheath, said lens being transversable in a sealed manner at a location adjacent said piece.

11. A pacemaker lead system according to claim 1 wherein the covering structure comprises a movable element inserted in an opening preformed in said sheath at a location adjacent said piece.

12. A pacemaker lead system according to claim 1 wherein a second spiral conductor is provided coaxial to said first conductor.

13. A pacemaker lead system according to claim 1 wherein a second spiral conductor is provided parallel to said first conductor.

14. A pacemaker lead system according to claim 1 wherein said access means comprises a preformed opening in said sealed covering structure.

15. A pacemaker lead system according to claim 14 wherein said covering structure comprises resilient material; and said opening comprises a preformed slit which is normally closed by said resilient material.

16. A pacemaker lead system according to claim 1 wherein said piece is rigid metal.

17. A pacemaker lead system, comprising:

a flexible spiral electrical conductor having first and second connector means at opposite ends thereof for removably connecting said conductor to a pulse generator and to an electrode stimulation device, respectively;

a resilient insulating sheath surrounding said conductor;

a piece of a rigid electrically conducting material electrically connected to said conductor and covered by said sheath; and a preformed access opening means, formed in said sheath adjacent said piece, for sealing said piece when closed and for being transversed by an auxiliary electrical connector in a sealed manner to connect an auxiliary electrical circuit to said piece without penetrating material of said piece.

18. A pacemaker lead system according to claim 17 wherein a movable closing element is provided in said access opening means.

19. A pacemaker lead system according to claim 17 wherein said access opening means comprises a slit normally closed by said resilient sheath.

* * * * *